United States Patent
Dyballa et al.

(10) Patent No.: US 9,221,851 B2
(45) Date of Patent: Dec. 29, 2015

(54) MIXTURE CONTAINING A MONOPHOSPHITE LIGAND AND THE USE THEREOF FOR CATALYSIS OF A HYDROFORMYLATION REACTION

(71) Applicants: Katrin Marie Dyballa, Recklinghausen (DE); Robert Franke, Marl (DE); Frank Geilen, Haltern am See (DE); Dieter Hess, Marl (DE); Dirk Fridag, Haltern am See (DE)

(72) Inventors: Katrin Marie Dyballa, Recklinghausen (DE); Robert Franke, Marl (DE); Frank Geilen, Haltern am See (DE); Dieter Hess, Marl (DE); Dirk Fridag, Haltern am See (DE)

(73) Assignee: EVONIK INDUSTRIES AG, Essen (DE)

( * ) Notice: Subject to any disclaimer, the term of this patent is extended or adjusted under 35 U.S.C. 154(b) by 0 days.

(21) Appl. No.: 14/716,470

(22) Filed: May 19, 2015

(65) Prior Publication Data
US 2015/0336989 A1 Nov. 26, 2015

(30) Foreign Application Priority Data
May 20, 2014 (DE) .......................... 10 2014 209 533

(51) Int. Cl.
| | | |
|---|---|---|
| *C07F 15/00* | (2006.01) | |
| *C07C 45/50* | (2006.01) | |
| *B01J 31/22* | (2006.01) | |
| *C07F 9/141* | (2006.01) | |

(52) U.S. Cl.
CPC ............. *C07F 9/141* (2013.01); *B01J 31/2221* (2013.01); *C07C 45/505* (2013.01); *C07F 15/0073* (2013.01)

(58) Field of Classification Search
CPC ... C07F 9/141; C07F 15/0073; C07C 45/505; B01J 31/2221
USPC ............................... 556/13; 558/197; 568/454
See application file for complete search history.

(56) References Cited

U.S. PATENT DOCUMENTS

| | | |
|---|---|---|
| 6,403,837 B1 | 6/2002 | Hess et al. |
| 2011/0230620 A1 | 9/2011 | Tunge et al. |
| 2012/0253080 A1 | 10/2012 | Eisenschmid et al. |
| 2014/0309423 A1 | 10/2014 | Christiansen et al. |

FOREIGN PATENT DOCUMENTS

| | | |
|---|---|---|
| DE | 10 2011 085 883 A1 | 5/2013 |
| EP | 0 614 870 A2 | 9/1994 |
| EP | 0 614 870 A3 | 9/1994 |
| EP | 1 099 678 A1 | 5/2001 |
| WO | WO 2010/057099 A1 | 5/2010 |

OTHER PUBLICATIONS

Selent, D., et al., "New Phosphorus Ligands for the Rhodium-Catalyzed Isomerization/Hydroformylation of Internal Octenes," *Angew. Chem. Int. Ed.*, 2001, vol. 40, No. 9, pp. 1696-1698.
Franke, R., et al., "Applied Hydroformylation," *Chem. Rev.*, 2012, vol. 112, pp. 5675-5732.
Selent, D., et al., "Novel Oxyfunctionalized Phosphonite Ligands for the Hydroformylation of Isomeric n-Olefins," *Angew. Chem. Int ed.*, 2000, vol. 39, No. 9, pp. 1639-1641.
European Search Report issued Aug. 6, 2015 in Patent Application No. 15166039.6 (with English translation of categories of cited documents).
Rui M.B. Carrilho, et al., "Rhodium/tris-binaphthyl chiral monophosphite complexes: Efficient catalysts for the hydroformylation of disubstituted aryl olefins" Journal of Organometallic Chemistry, vol. 698, XP028392107, 2012, pp. 28-34.
Konstantin N. Gavrilov, et al., "Phosphites and diamidophosphites based on mono-ethers of BINOL: a comparison of enantioselectivity in asymmetric catalytic reactions" Tetrahedron, vol. 68, XP028436933, 2012, pp. 1581-1589.
Ana Z. Gonzalez, et al., "Gold(I)-Catalyzed Enantioselective [4 + 2]Cycloaddition of Allene-dienes" Organic Letters, vol. 12, No. 1, XP055201269, 2010, pp. 200-203.

*Primary Examiner* — Porfirio Nazario Gonzalez
(74) *Attorney, Agent, or Firm* — Oblon, McClelland, Maier & Neustadt, L.L.P.

(57) ABSTRACT

A mixture containing a monophosphite ligand is useful for the catalysis of a hydroformylation reaction.

20 Claims, No Drawings

MIXTURE CONTAINING A MONOPHOSPHITE LIGAND AND THE USE THEREOF FOR CATALYSIS OF A HYDROFORMYLATION REACTION

BACKGROUND OF THE INVENTION

1. Field of the Invention

The invention relates to a mixture containing a monophosphite ligand and the use thereof for catalysis of a hydroformylation reaction.

2. Discussion of the Background

The reactions between olefin compounds, carbon monoxide and hydrogen in the presence of a catalyst to give the aldehydes comprising one additional carbon atom are known as hydroformylation or oxo synthesis. The catalysts used in these reactions are frequently compounds of the transition metals of group VIII of the Periodic Table of the Elements. Known ligands are, for example, compounds from the classes of the phosphines, phosphites and phosphonites, each with trivalent phosphorus $P^{III}$. A good overview of the state of the hydroformylation of olefins can be found in B. CORNILS, W. A. HERRMANN, "Applied Homogeneous Catalysis with Organometallic Compounds", vol. 1 & 2, VCH, Weinheim, New York, 1996 or R. Franke, D. Selent, A. Börner, "Applied Hydroformylation", Chem. Rev., 2012, DOI:10.1021/cr3001803.

The type of catalyst system and the optimal reaction conditions for the hydroformylation are dependent on the reactivity of the olefin used.

The different reactivity of isomeric octenes is likewise known (see B. L. Haymore, A. van Hassell, R. Beck, Annals of the New York Acad. Sci., 415, 1983, p. 159-175).

Via the different processes and catalysts, a multitude of olefins are available for the hydroformylation (see P. W. N. M. van Leeuwen, in Rhodium Catalyzed Hydroformylation, P. W. N. M. van Leeuwen, C. Claver (eds.), Kluwer, Dordrecht, 2000).

Technical olefin mixtures which are used as reactants for the oxo process often contain olefins of a wide variety of different structures, having different levels of branching, different double bond positions in the molecule and possibly also different carbon numbers. This is particularly true of olefin mixtures which have formed through di-, tri- or substantial oligomerization of olefins. Examples of technical olefin mixtures which are converted to the corresponding aldehyde mixtures by hydroformylation include tri- and tetrapropene, and di-, tri- and tetrabutene.

The abovementioned technical olefin mixtures often contain only small proportions of olefins having terminal double bonds. In order to prepare products in which more terminally hydroformylated aldehyde is present than in the original olefin mixture therefrom, it is necessary to hydroformylate under isomerizing conditions.

Suitable processes for this purpose are, for example, high-pressure hydroformylations with cobalt catalysts. However, disadvantages of these processes include the fact that a relatively large number of by-products such as alkanes, acetals and ethers are formed and that very severe reaction conditions (high temperature, high pressure) are necessary (see also Klaus-Diether Wiese, Dietmar Obst, Top. Organomet. Chem. 2006, 18, 1-33).

When rhodium complexes are used as catalyst, the ligand is another crucial factor for the product composition of the aldehydes. Unmodified rhodium-carbonyl complexes catalyse the hydroformylation of olefins having terminal and internal double bonds, where the olefins may also be branched, to give aldehydes having a high level of branching. The proportion of terminally hydroformylated olefin is much lower compared to the cobalt-catalysed product.

The hydroformylation of olefins having internal double bonds over catalyst systems containing sterically demanding bisphosphite ligands proceeds with good selectivity in the case of long-chain olefins, but with an unsatisfactory activity (P. W. N. M. van Leeuwen, in Rhodium Catalyzed Hydroformylation, P. W. N. M. van Leeuwen, C. Claver (eds.), Kluwer, Dordrecht, 2000).

In Angew. Chem. Int. Ed. 2000, 39, No. 9, p. 1639-1641 by Börner et al., phosphonites are used in hydroformylation, i.e. ligands having one P—C and two P—O bonds. The phosphonites described here, when used in hydroformylation, have n/iso selectivity (n/iso=the ratio of linear aldehyde (=n) to branched (=iso) aldehyde)) of 0.61 to 1.57.

However, the preparation of these ligands based on a phosphorite structure, in the case of an industrial-scale synthesis, is much more complex than, for example, the preparation of phosphite ligands. This point is a crucial factor especially in the case of use of these ligands in an industrial scale process. The synthesis of the compounds used as ligands should be as inexpensive and simple as possible.

Rhodium-monophosphite complexes in catalytically active compositions, in contrast, are suitable for the hydroformylation of branched olefins having internal double bonds.

Since the 1970s, there have been descriptions of the use of "bulky phosphites" in hydroformylation (see, inter alia, van Leeuwen et al., Journal of Catalysis, 2013, 298, 198-205). These feature good activity, but the n/i selectivity for terminally hydroformylated compounds is in need of improvement.

As well as the use of pure ligands, the use of ligand mixtures has also been described in the literature.

US 20120253080 describes the use of monophosphites with bisphosphites. However, this combination has the disadvantage that the bisphosphites, although having good selectivity, have very low activity in the case of long-chain olefins and are therefore in need of improvement. In an industrial scale process, in addition to the selectivity for the desired product, the space-time yield or the activity of the catalyst system is also an important factor with regard to the economic viability thereof. Moreover, the bisphosphites are frequently much more costly to prepare than, for example, monophosphites.

EP 1 099 678 describes the use of phosphonites with bisphosphites. However, it is disadvantageous here that both ligand types are very costly to produce, and an industrial scale process can therefore hardly be economically viable. Moreover, the addition of the bisphosphite ligand noticeably affects the yield of the reaction, since these ligands are less active when dibutene, for example, is used as substrate.

It is therefore desirable to develop a catalyst system which does not have the disadvantages exhibited in the related art.

SUMMARY OF THE INVENTION

It was therefore an object of the present invention to provide a catalyst system for hydroformylation of olefins, with which branched, unbranched, terminal and internal olefins can be terminally hydroformylated with high yields and selectivities, i.e. very substantially linear aldehydes can be prepared.

In addition, the cost/benefit ratio of the ligands being used is to be optimized.

This and other objects are achieved by the present invention which in pone embodiment relates to a mixture, comprising:

at least one of the two compounds of the structures Ia and Ib:

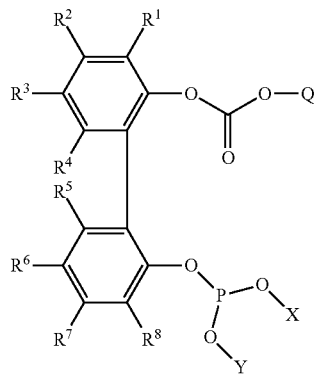

Ia

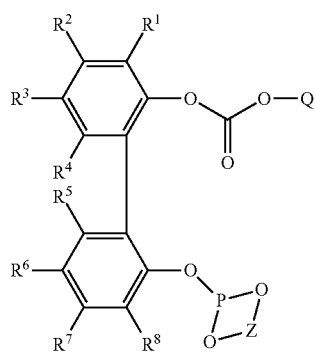

Ib wherein $R^1$, $R^2$, $R^3$, $R^4$, $R^5$, $R^6$, $R^7$, $R^8$ are each independently selected from the group consisting of:

—H, —$(C_1\text{-}C_{12})$-alkyl, —O—$(C_1\text{-}C_{12})$-alkyl, —O—$(C_6\text{-}C_{20})$-aryl, —$(C_6\text{-}C_{20})$-aryl, halogen, COO—$(C_1\text{-}C_{12})$-alkyl, CONH—$(C_1\text{-}C_{12})$-alkyl, —$(C_6\text{-}C_{20})$-aryl-CON[$(C_1\text{-}C_{12})$-alkyl]$_2$, —CO—$(C_1\text{-}C_{12})$-alkyl, —CO—$(C_6\text{-}C_{20})$-aryl, —COOH, —OH, —$SO_3H$, —$SO_3Na$, —$NO_2$, —CN, —$NH_2$, and —N[$(C_1\text{-}C_{12})$-alkyl]$_2$;

X and Y are each independently selected from the group consisting of:

—$(C_1\text{-}C_{12})$-alkyl, —$(C_6\text{-}C_{20})$-aryl, —$(C_6\text{-}C_{20})$-aryl-$(C_1\text{-}C_{12})$-alkyl, —$(C_6\text{-}C_{20})$-aryl-O—$(C_1\text{-}C_{12})$-alkyl, —$(C_1\text{-}C_{12})$-alkyl-$(C_6\text{-}C_{20})$-aryl, —$(C_6\text{-}C_{20})$-aryl-COO—$(C_1\text{-}C_{12})$-alkyl, —$(C_6\text{-}C_{20})$-aryl-CONH—$(C_1\text{-}C_{12})$-alkyl, —$(C_6\text{-}C_{20})$-aryl-CON[$(C_1\text{-}C_{12})$-alkyl]$_2$, —$(C_4\text{-}C_{20})$-heteroaryl, —$(C_4\text{-}C_2O$-heteroaryl-$(C_1\text{-}C_{12})$-alkyl, and —$(C_5\text{-}C_8)$-cycloalkyl-$(C_4\text{-}C_{20})$-aryl-CO—$(C_6\text{-}C_{20})$-aryl, Z is selected from the group consisting of:

—$(C_1\text{-}C_{12})$-alkyl-, —$(C_6\text{-}C_{20})$-aryl-, —$(C_6\text{-}C_{20})$-aryl-$(C_1\text{-}C_{12})$-alkyl-, —$(C_1\text{-}C_{12})$-alkyl-$(C_6\text{-}C_{20})$-aryl-, —$(C_4\text{-}C_{20})$-heteroaryl-, —$(C_6\text{-}C_{20})$-aryl-CO—$(C_6\text{-}C_{20})$-aryl-, and —$(C_6\text{-}C_{20})$-aryl-$(C_6\text{-}C_{20})$-aryl-;

Q is selected from the group consisting of:

—$(C_1\text{-}C_{18})$-alkyl-, —$(C_1\text{-}C_{12})$-alkyl-$(C_1\text{-}C_{20})$-aryl-, —$(C_1\text{-}C_{18})$-haloalkyl-, and —NH—$(C_1\text{-}C_{18})$-alkyl, wherein the alkyl, heteroalkyl, cycloalkyl, heterocloalkyl, aryl and heteroaryl groups are optionally substituted, and a compound of the structure IIa:

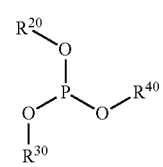

IIa wherein $R^{20}$, $R^{30}$, $R^{40}$ are each independently selected from the group consisting of:

—$(C_1\text{-}C_{12})$-alkyl, —$(C_6\text{-}C_{20})$-aryl, and —$(C_3\text{-}C_{12})$-cycloalkyl, two $R^{20}$ and $R^{30}$, or $R^{20}$ and $R^{40}$, or $R^{30}$ and $R^{40}$ radicals are optionally bridged to one another, and optionally have a —$(C_6\text{-}C_{20})$-aryl-$(C_6\text{-}C_{20})$-aryl unit, wherein the alkyl, cycloalkyl and aryl groups mentioned are optionally substituted.

In another embodiment, the present invention relates to a complex mixture, comprising:

the above mixture, and a metal atom selected from the group consisting of Rh, Ru, Co, and Ir.

In yet another embodiment, the present invention relates to a process of hydroformylating an olefin, comprising:

a) initially charging an olefin;

b) adding the above complex mixture, or a mixture as described above and a compound comprising a metal atom selected from the group consisting of Rh, Ru, Co, and Ir, to obtain a reaction mixture;

c) feeding $H_2$ and CO into the reaction mixture, d) heating the reaction mixture, to obtain conversion of the olefin to an aldehyde.

DETAILED DESCRIPTION OF THE INVENTION

The present invention relates to a mixture comprising at least one of the two compounds of the structures Ia and Ib:

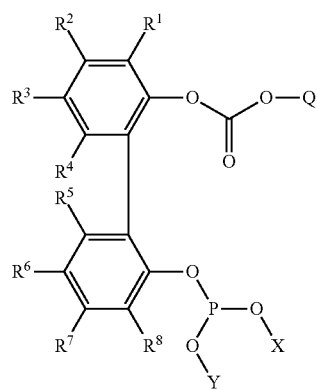

Ia

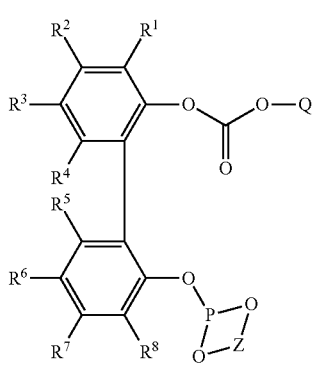
Ib where
R¹, R², R³, R⁴, R⁵, R⁶, R⁷, R⁸ are each independently selected from:
—H, —(C₁-C₁₂)-alkyl, —O—(C₁-C₁₂)-alkyl, —O—(C₆-C₂₀)-aryl, —(C₆-C₂₀)-aryl, halogen, COO—(C₁-C₁₂)-alkyl, CONH—(C₁-C₁₂)-alkyl, —(C₆-C₂₀)-aryl-CON[(C₁-C₁₂)-alkyl]₂, —COO—(C₁-C₁₂)-alkyl, —CO—(C₆-C₂₀)-aryl, —COOH, —OH, —SO₃H, —SO₃Na, —NO₂, —CN, —NH₂, —N[(C₁-C₁₂)-alkyl]₂;

X and Y are each independently selected from:
—(C₁-C₁₂)-alkyl, —(C₆-C₂₀)-aryl, —(C₆-C₂O-aryl-(C₁-C₁₂)-alkyl, —(C₆-C₂₀)-aryl-O—(C₁-C₁₂)-alkyl, —(C₁-C₁₂)-alkyl-(C₆-C₂₀)-aryl, —(C₆-C₂₀)-aryl-COO—(C₁-C₁₂)-alkyl, —(C₆-C₂₀)-aryl-CONH—(C₁-C₁₂)-alkyl, —(C₆-C₂₀)-aryl-CON[(C₁-C₁₂)-alkyl]₂, —(C₄-C₂₀)-heteroaryl, —(C₄-C₂₀)-heteroaryl-(C₁-C₁₂)-alkyl, —(C₅-C₈)-cycloalkyl-(C₄-C₂₀)-aryl-CO—(C₆-C₂₀)-aryl, Z is selected from:
—(C₁-C₁₂)-alkyl-, —(C₆-C₂₀)-aryl-, —(C₆-C₂O-aryl-(C₁-C₁₂)-alkyl-, —(C₁-C₁₂)-alkyl-(C₆-C₂₀)-aryl-, —(C₄-C₂₀)-heteroaryl-, —(C₆-C₂₀)-aryl-CO—(C₆-C₂₀)-aryl-, —(C₆-C₂₀)-aryl-(C₆-C₂₀)-aryl-;

Q is selected from:
—(C₁-C₁₈)-alkyl-, —(C₁-C₁₈)-haloalkyl-, —NH—(C₁-C₁₈)-alkyl,
where the alkyl, heteroalkyl, cycloalkyl, heterocycloalkyl, aryl and heteroaryl groups mentioned may be substituted;
and a compound of the structure IIa:

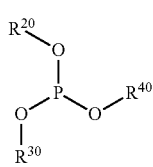
IIa where
R²⁰, R³⁰, R⁴⁰ are each independently selected from:
—(C₁-C₁₂)-alkyl, —(C₆-C₂₀)-aryl, —(C₃-C₁₂)-cycloalkyl, two R²⁰ and R³⁰ or R²⁰ and R⁴⁰ or R³⁰ and R⁴⁰ radicals may also be bridged to one another, and may have a —(C₆-C₂₀)-aryl-(C₆-C₂₀)-aryl unit,
where the alkyl, cycloalkyl and aryl groups mentioned may be substituted.

With such a ligand mixture, it is possible to terminally hydroformylate branched, unbranched, terminal and internal olefins with high yields and selectivities, i.e. to prepare linear aldehydes.

Through the use of the inventive ligand mixture, it is possible to control the selectivity of the product.

(C₁-C₁₂)-Alkyl and O—(C₁-C₁₂)-alkyl may each be unsubstituted or substituted by one or more identical or different radicals selected from (C₃-C₁₂)-cycloalkyl, (C₃-C₁₂)-heterocycloalkyl, (C₆-C₂₀)-aryl, fluorine, chlorine, cyano, formyl, acyl and alkoxycarbonyl.

(C₃-C₁₂)-Cycloalkyl and (C₃-C₁₂)-heterocycloalkyl may each be unsubstituted or substituted by one or more identical or different radicals selected from (C₁-C₁₂)-alkyl, (C₁-C₁₂)-alkoxy, (C₃-C₁₂)-cycloalkyl, (C₃-C₁₂)-heterocycloalkyl, (C₆-C₂₀)-aryl, fluorine, chlorine, cyano, formyl, acyl and alkoxycarbonyl.

(C₆-C₂₀)-Aryl and —(C₆-C₂₀)-aryl-(C₆-C₂₀)-aryl- may each be unsubstituted or substituted by one or more identical or different radicals selected from —H, —(C₁-C₁₂)-alkyl, —O—(C₁-C₁₂)-alkyl, —O—(C₆-C₂₀)-aryl, —(C₆-C₂₀)-aryl, -halogen (such as Cl, F, Br, I), —COO—(C₁-C₁₂)-alkyl, —CONH—(C₁-C₁₂)-alkyl, —(C₆-C₂₀)-aryl-CON[(C₁-C₁₂)-alkyl]₂, —CO—(C₁-C₁₂)-alkyl, —CO—(C₆-C₂₀)-aryl, —COOH, —OH, —SO₃H; —SO₃Na, —NO₂, —CN, —NH₂, —N[(C₁-C₁₂)-alkyl]₂.

All ranges mentioned herein include all values and subvalues between the lower and upper limits of the range.

In the context of the invention, the expression —(C₁-C₁₂)-alkyl encompasses straight-chain and branched alkyl groups. Preferably, these groups are unsubstituted straight-chain or branched —(C₁-C₈)-alkyl groups and most preferably —(C₁-C₆)-alkyl groups. Examples of (C₁-C₁₂)-alkyl groups are especially methyl, ethyl, propyl, isopropyl, n-butyl, isobutyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1,1,2-trimethylpropyl, 1,2,2-trimethylpropyl, 1-ethylbutyl, 1-ethyl-2-methylpropyl, n-heptyl, 2-heptyl, 3-heptyl, 2-ethylpentyl, 1-propylbutyl, n-octyl, 2-ethythexyl, 2-propylheptyl, nonyl, decyl.

The elucidations relating to the expression —(C₁-C₁₂)-alkyl also apply to the alkyl groups in —O—(C₁-C₁₂)-alkyl, i.e. in —(C₁-C₁₂)-alkoxy. Preferably, these groups are unsubstituted straight-chain or branched —(C₁-C₆)-alkoxy groups.

Substituted —(C₁-C₁₂)-alkyl groups and substituted —(C₁-C₁₂)-alkoxy groups may have one or more substituents, depending on their chain length. The substituents are preferably each independently selected from —(C₃-C₁₂)-cycloalkyl, —(C₃-C₁₂)-heterocycloalkyl, —(C₆-C₂₀)-aryl, fluorine, chlorine, cyano, formyl, acyl and alkoxycarbonyl.

The expression "—(C₃-C₁₂)-cycloalkyl", in the context of the present invention, encompasses mono-, bi- or tricyclic hydrocarbyl radicals having 3 to 12, especially 5 to 12, carbon atoms. These include cyclopropyl, cyclobutyl, cyclopentyl, cyclohexyl, cycloheptyl, cyclooctyl, cyclododecyl, cyclopentadecyl, norbonyl and adamantyl.

The expression "—(C₃-C₁₂)-heterocycloalkyl groups", in the context of the present invention, encompasses nonaromatic saturated or partly unsaturated cycloaliphatic groups having 3 to 12, especially 5 to 12, carbon atoms. The —(C₃-C₁₂)-heterocycloalkyl groups have preferably 3 to 8, more preferably 5 or 6, ring atoms. In the heterocycloalkyl groups, as opposed to the cycloalkyl groups, 1, 2, 3 or 4 of the ring carbon atoms are replaced by heteroatoms or heteroatom-containing groups. The heteroatoms or the heteroatom-containing groups are preferably selected from —O—, —S—, —N—, —N(=O)—, —C(=O)— and —S(=O)—.

Examples of —($C_3$-$C_{12}$)-heterocycloalkyl groups are tetrahydrothiophenyl, tetrahydrofuryl, tetrahydropyranyl and dioxanyl.

Substituted —($C_3$-$C_{12}$)-cycloalkyl groups and substituted —($C_3$-$C_{12}$)-heterocycloalkyl groups may have one or more (e.g. 1, 2, 3, 4 or 5) further substituents, depending on their ring size. These substituents are preferably each independently selected from —($C_1$-$C_{12}$)-alkyl, —($C_1$-$C_{12}$)-alkoxy, —($C_3$-$C_{12}$)-cycloalkyl, —($C_3$-$C_{12}$)-heterocycloalkyl, —($C_6$-$C_{20}$)-aryl, fluorine, chlorine, cyano, formyl, acyl and alkoxycarbonyl. Substituted —($C_3$-$C_{12}$)-cycloalkyl groups preferably bear one or more —($C_1$-$C_6$)-alkyl groups. Substituted —($C_3$-$C_{12}$)-heterocycloalkyl groups preferably bear one or more —($C_1$-$C_6$)-alkyl groups.

In the context of the present invention, the expression —($C_6$-$C_{20}$)-aryl and —($C_6$-$C_{20}$)-aryl-($C_6$-$C_{20}$)-aryl- encompasses mono- or polycyclic aromatic hydrocarbyl radicals. These have 6 to 20 ring atoms, more preferably 6 to 14 ring atoms, especially 6 to 10 ring atoms. Aryl is preferably —($C_6$-$C_{10}$)-aryl and —($C_6$-$C_{10}$)-aryl-($C_6$-$C_{10}$)-aryl-. Aryl is especially phenyl, naphthyl, indenyl, fluorenyl, anthracenyl, phenanthrenyl, naphthacenyl, chrysenyl, pyrenyl, coronenyl. More particularly, aryl is phenyl, naphthyl and anthracenyl.

Substituted —($C_6$-$C_{20}$)-aryl groups and —($C_6$-$C_{20}$)-aryl-($C_6$-$C_{20}$)-aryl groups may have one or more (e.g. 1, 2, 3, 4 or 5) substituents, depending on the ring size. These substituents are preferably each independently selected from —H, —($C_1$-$C_{12}$)-alkyl, —O—($C_1$-$C_{12}$)-alkyl, —O—($C_6$-$C_{20}$)-aryl, —($C_6$-$C_{20}$)-aryl, -halogen (such as Cl, F, Br, I), —COO—($C_1$-$C_{12}$)-alkyl, —CONH—($C_1$-$C_{12}$)-alkyl, —($C_6$-$C_{20}$)-aryl-CON[($C_1$-$C_{12}$)-alkyl]$_2$, —CO—($C_1$-$C_{12}$)-alkyl, —CO—($C_6$-$C_{20}$)-aryl, —COOH, —OH, —$SO_3H$, —$SO_3Na$, —$NO_2$, —CN, —$NH_2$, —N[($C_1$-$C_{12}$)-alkyl]$_2$.

Substituted —($C_6$-$C_{20}$)-aryl groups and —($C_6$-$C_{20}$)-aryl-($C_6$-$C_{20}$)-aryl groups are preferably substituted —($C_6$-$C_{10}$)-aryl groups and —($C_6$-$C_{10}$)-aryl-($C_6$-$C_{10}$)-aryl groups, especially substituted phenyl or substituted naphthyl. Substituted —($C_6$-$C_{20}$)-aryl groups preferably bear one or more, for example 1, 2, 3, 4 or 5, substituents selected from —($C_1$-$C_{12}$)-alkyl groups, —($C_1$-$C_{12}$)-alkoxy groups.

In one embodiment, Q is selected from:
—($C_1$-$C_{12}$)-alkyl-, —($C_1$-$C_{18}$)-haloalkyl-, —NH—($C_1$-$C_8$)-alkyl.

In one embodiment, the mixture comprises at least one of the two compounds of the structures Ic and Id:

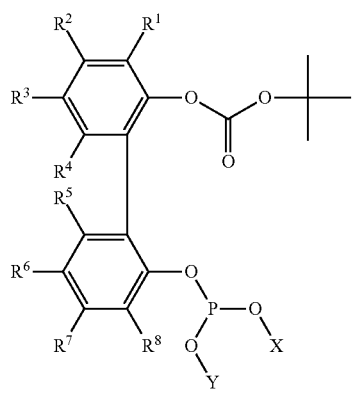

Ic

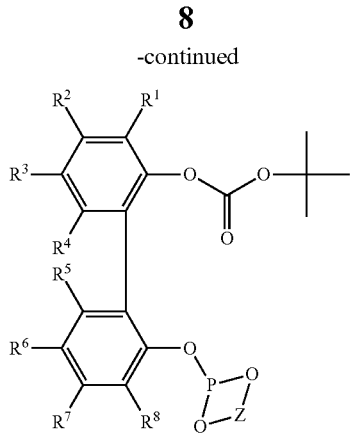

Id

In one embodiment, X and Y are each independently selected from:
—($C_1$-$C_{12}$)-alkyl, —($C_6$-$C_{20}$)-aryl, —($C_6$-$C_{20}$)-aryl-($C_1$-$C_{12}$)-alkyl, —($C_6$-$C_{20}$)-aryl-O—($C_1$-$C_{12}$)-alkyl, —($C_6$-$C_{20}$)-aryl-COO—($C_1$-$C_{12}$)-alkyl, —($C_6$-$C_{20}$)-aryl-CONH—($C_1$-$C_{12}$)-alkyl, —($C_6$-$C_{20}$)-aryl-CON[($C_1$-$C_{12}$)-alkyl]$_2$, —($C_4$-$C_{20}$)-heteroaryl, —($C_4$-$C_{20}$)-heteroaryl-($C_1$-$C_{12}$)-alkyl.

In one embodiment, X and Y are each independently selected from:
—($C_1$-$C_{12}$)-alkyl, —($C_6$-$C_{20}$)-aryl, —($C_6$-$C_{20}$)-aryl-($C_1$-$C_{12}$)-alkyl, —($C_6$-$C_{20}$)-aryl-O—($C_1$-$C_{12}$)-alkyl, —($C_6$-$C_{20}$)-aryl-COO—($C_1$-$C_{12}$)-alkyl.

In one embodiment, Z is selected from:
—($C_1$-$C_{12}$)-alkyl-, —($C_6$-$C_{20}$)-aryl-, —($C_6$-$C_{20}$)-aryl-($C_1$-$C_{12}$)-alkyl-, —($C_6$-$C_{20}$)-aryl-CO—($C_6$-$C_{20}$)-aryl-, —($C_1$-$C_{12}$)-alkyl-($C_6$-$C_{20}$)-aryl-, —($C_6$-$C_{20}$)-aryl-($C_6$-$C_{20}$)-aryl-.

In one embodiment, $R^1$, $R^2$, $R^3$, $R^4$, $R^5$, $R^6$, $R^7$, $R^8$ are each independently selected from:
—H, —($C_1$-$C_{12}$)-alkyl, —O—($C_1$-$C_{12}$)-alkyl, —O—($C_6$-$C_{20}$)-aryl, —($C_6$-$C_{20}$)-aryl, —COO—($C_1$-$C_{12}$)-alkyl, —CONH—($C_1$-$C_{12}$)-alkyl, —($C_6$-$C_{20}$)-aryl-CON[($C_1$-$C_{12}$)-alkyl]$_2$, —CO—($C_1$-$C_{12}$)-alkyl, —CO—($C_6$-$C_{20}$)-aryl, —COOH, —OH, —$NH_2$, —N[($C_1$-$C_{12}$)-alkyl]$_2$.

In one embodiment, X and Y are the same radicals.
In one embodiment, $R^3$ and $R^6$ are each —O—($C_1$-$C_{12}$)-alkyl.
In one embodiment, $R^3$ and $R^6$ are each —OMe.
In one embodiment, $R^1$ and $R^8$ are each —($C_1$-$C_{12}$)-alkyl.
In one embodiment, $R^1$ and $R^8$ are each tert-butyl.
In one embodiment, the mixture comprises a compound of the structure Ie:

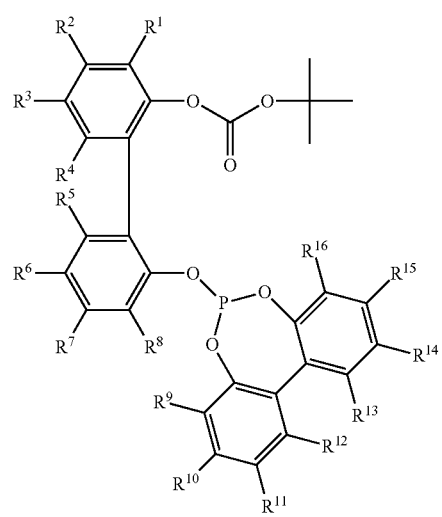

Ie where $R^9, R^{10}, R^{11}, R^{12}, R^{13}, R^{14}, R^{15}, R^{16}$ are each independently selected from:

—H, —$(C_1$-$C_{12})$-alkyl, —O—$(C_1$-$C_{12})$-alkyl, —O—$(C_6$-$C_{20})$-aryl, —$(C_6$-$C_{20})$-aryl, -halogen, —COO—$(C_1$-$C_{12})$-alkyl, —CONH—$(C_1$-$C_{12})$-alkyl, —$(C_6$-$C_{20})$-aryl-CON[$(C_1$-$C_{12})$-alkyl]$_2$, —CO—$(C_1$-$C_{12})$-alkyl, —CO—$(C_6$-$C_{20})$-aryl, —COOH, —OH, —$SO_3H$, —$SO_3Na$, —$NO_2$, —CN, —$NH_2$, —N[$(C_1$-$C_{12})$-alkyl]$_2$.

In one embodiment, the mixture comprises a compound of the structure If:

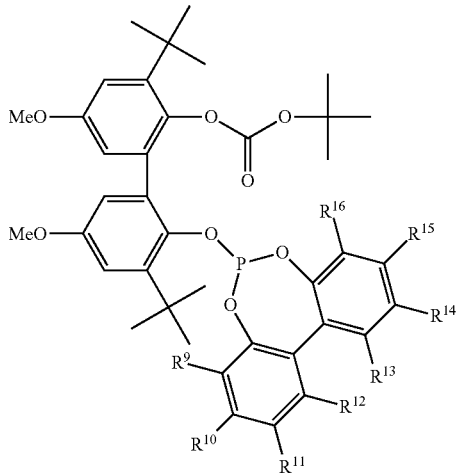

If where $R^9, R^{10}, R^{11}, R^{12}, R^{13}, R^{14}, R^{15}, R^{16}$ are each independently selected from:

—H, —$(C_1$-$C_{12})$-alkyl, —O—$(C_1$-$C_{12})$-alkyl, —O—$(C_6$-$C_{20})$-aryl, —$(C_6$-$C_{20})$-aryl, -halogen, —COO—$(C_1$-$C_{12})$-alkyl, —CONH—$(C_1$-$C_{12})$-alkyl, —$(C_6$-$C_{20})$-aryl-CON[$(C_1$-$C_{12})$-alkyl]$_2$, —CO—$(C_6$-$C_{20})$-aryl, —COOH, —OH, —$SO_3H$, —$SO_3Na$, —$NO_2$, —CN, —$NH_2$, —N[$(C_1$-$C_{12})$-alkyl]$_2$.

In one embodiment, $R^{20}, R^{30}, R^{40}$ are each independently selected from: —$(C_1$-$C_{12})$-alkyl, —$(C_6$-$C_{20})$-aryl, where the alkyl and aryl groups mentioned may be substituted.

In one embodiment, the mixture comprises a compound of the structure IIb:

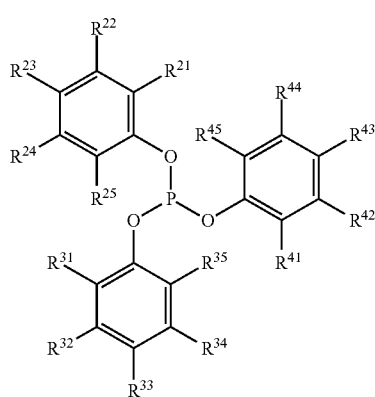

IIb where
$R^{21}, R^{22}, R^{23}, R^{24}, R^{25}, R^{31}, R^{32}, R^{33}, R^{34}, R^{35}, R^{41}, R^{42}, R^{43}, R^{44}, R^{45}$ are each independently selected from:

—H, —$(C_1$-$C_{12})$-alkyl, —O—$(C_1$-$C_{12})$-alkyl, —O—$(C_6$-$C_{20})$-aryl, —$(C_6$-$C_{20})$-aryl, -halogen, —COO—$(C_1$-$C_{12})$-alkyl, —CONH—$(C_1$-$C_{12})$-alkyl, —$(C_6$-$C_{20})$-aryl-CON[$(C_1$-$C_{12})$-alkyl]$_2$, —CO—$(C_1$-$C_{12})$-alkyl, —CO—$(C_6$-$C_{20})$-aryl, —COOH, —OH, —$SO_3H$, —$SO_3Na$, —$NO_2$, —CN, —$NH_2$, —N[$(C_1$-$C_{12})$-alkyl]$_2$.

In one embodiment, $R^{21}, R^{22}, R^{23}, R^{24}, R^{25}, R^{31}, R^{32}, R^{33}, R^{34}, R^{35}, R^{41}, R^{42}, R^{43}, R^{44}, R^{45}$ are each independently selected from:

—H, —$(C_1$-$C_{12})$-alkyl, —O—$(C_1$-$C_{12})$-alkyl, —O—$(C_6$-$C_{20})$-aryl, —$(C_6$-$C_{20})$-aryl, —$SO_3H$, —$SO_3Na$, —$NH_2$, —N[$(C_1$-$C_{12})$-alkyl]$_2$.

In one embodiment, $R^{21}, R^{22}, R^{23}, R^{24}, R^{25}, R^{31}, R^{32}, R^{33}, R^{34}, R^{35}, R^{41}, R^{42}, R^{43}, R^{44}, R^{45}$ are each independently selected from:

—H, —$(C_1$-$C_{12})$-alkyl, —O—$(C_1$-$C_{12})$-alkyl, —O—$(C_6$-$C_{20})$-aryl, —$(C_6$-$C_{20})$-aryl.

In one embodiment, $R^{21}, R^{31}, R^{41}$ are each tert-butyl.
In one embodiment, $R^{23}, R^{33}, R^{43}$ are each tert-butyl.
In one embodiment, $R^{23}, R^{33}, R^{43}$ are each methyl.

As well as the mixture, a complex mixture including such a mixture is also claimed.

Complex mixture comprising:
an above-described mixture,
a metal atom selected from: Rh, Ru, Co, Ir.

In the complex mixture, three different cases may exist:
1) The complex has ligands either of the I or II type, and the mixture is of complex molecules having only ligands of the I type with complex molecules having only ligands of the II type.
2) A complex in itself already has ligands of the I and II type.
3) Is a mixed form of 1) and 2).

As well as the mixtures/complex mixtures, also claimed is the use thereof as complex mixtures for catalysis of a hydroformylation reaction. In this case, the compounds in the mixture are the ligands in the complex. The ligands coordinate to the central metal atom. The ligand-metal complex thus obtained or the complex mixtures thus obtained then catalyse the hydroformylation reaction.

Use of an above-described mixture in a complex mixture for catalysis of a hydroformylation reaction.

In addition, also claimed is the hydroformylation reaction in which the mixtures or complex mixtures are used.

Process comprising the process steps of:
a) initially charging an olefin,
b) adding an above-described complex mixture,
or an above-described mixture and a compound including a metal atom selected from: Rh, Ru, Co, Ir,
c) feeding in $H_2$ and CO,
d) heating the reaction mixture, with conversion of the olefin to an aldehyde.

In this process, process steps a) to d) can be effected in any desired sequence.

In a preferred embodiment, the metal is Rh.

The reactants for the hydroformylation in the process of the invention are olefins or mixtures of olefins, especially monoolefins having 2 to 24, preferably 3 to 16 and more preferably 3 to 12 carbon atoms, having terminal or internal C—C double bonds, for example 1-propene, 1-butene, 2-butene, 1- or 2-pentene, 2-methyl-1-butene, 2-methyl-2-butene, 3-methyl-1-butene, 1-, 2- or 3-hexene, the $C_6$ olefin mixture obtained in the dimerization of propene (dipropene), heptenes, 2- or 3-methyl-1-hexenes, octenes, 2-methylheptenes, 3-methylheptenes, 5-methyl-2-heptene, 6-methyl-2-heptene, 2-ethyl-1-hexene, the $C_8$ olefin mixture obtained in the dimerization of butenes (di-n-butene, diisobutene), nonenes, 2- or 3-methyloctenes, the $C_9$ olefin mixture obtained in the trimerization of propene (tripropene), decenes, 2-ethyl-1-octene, dodecenes, the $C_{12}$ olefin mixture obtained in the tetramerization of propene or the trimerization of butenes (tetrapropene or tributene), tetradecenes, hexadecenes, the $C_{16}$ olefin mixture obtained in the tetramerization of butenes (tetrabutene), and olefin mixtures prepared by cooligomerization of olefins having different numbers of carbon atoms (preferably 2 to 4).

The process according to the invention using the mixtures/complex mixtures according to the invention can be used to hydroformylate α-olefins, terminally branched, internal and internally branched olefins. What is remarkable is the high yield of terminally hydroformylated olefin, even when only a small proportion of olefins having a terminal double bond was present in the reactant.

The invention is to be illustrated in detail hereinafter by working examples.

Having generally described this invention, a further understanding can be obtained by reference to certain specific examples which are provided herein for purposes of illustration only, and are not intended to be limiting unless otherwise specified.

EXAMPLES

General Operating Procedures

All the preparations which follow were carried out under protective gas using standard Schlenk techniques. The solvents were dried over suitable desiccants before use (Purification of Laboratory Chemicals, W. L. F. Armarego, Christina Chai, Butterworth Heinemann (Elsevier), 6th edition, Oxford 2009).

All preparative operations were effected in baked-out vessels. The products were characterized by means of NMR spectroscopy. Chemical shifts (δ) are reported in ppm. The $^{31}P$ NMR signals were referenced according to: $SR_{31P}=SR_{1H}*(BF_{31P}/BF_{1H})=SR_{1H}*0.4048$. (Robin K. Harris, Edwin D. Becker, Sonia M. Cabral de Menezes, Robin Goodfellow, and Pierre Granger, Pure Appl. Chem., 2001, 73, 1795-1818; Robin K. Harris, Edwin D. Becker, Sonia M. Cabral de Menezes, Pierre Granger, Roy E. Hoffinan and Kurt W. Zilm, Pure Appl. Chem., 2008, 80, 59-84).

Nuclear resonance spectra were recorded by means of a Bruker Avance 300 or Bruker Avance 400; gas chromatography analysis was effected using an Agilent GC 7890A.

The ligands according to the invention can be prepared here in various ways. Three possible ways are shown in the schemes which follow (A to C).

The reaction routes shown are merely illustrative and are shown in highly simplified form. Thus, if required, base can be used additionally in all the steps. In addition, the bases specified in the individual synthesis stages may be replaced by other commercially available bases known to those skilled in the art.

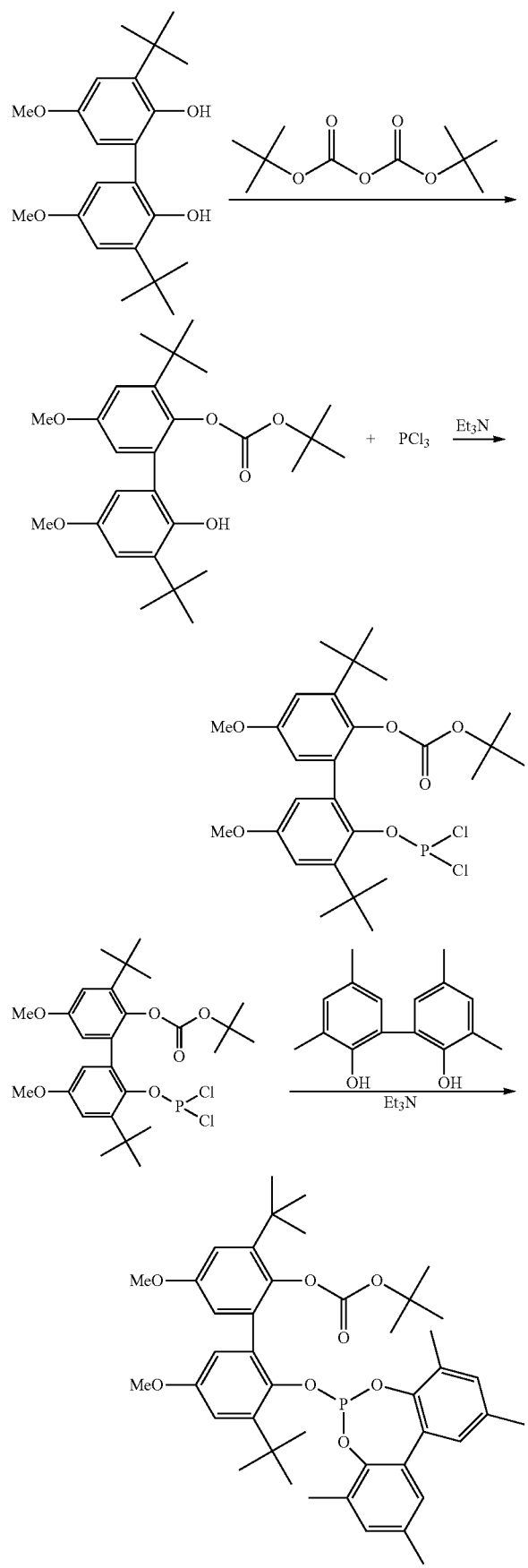

Reaction route A

Reaction route B
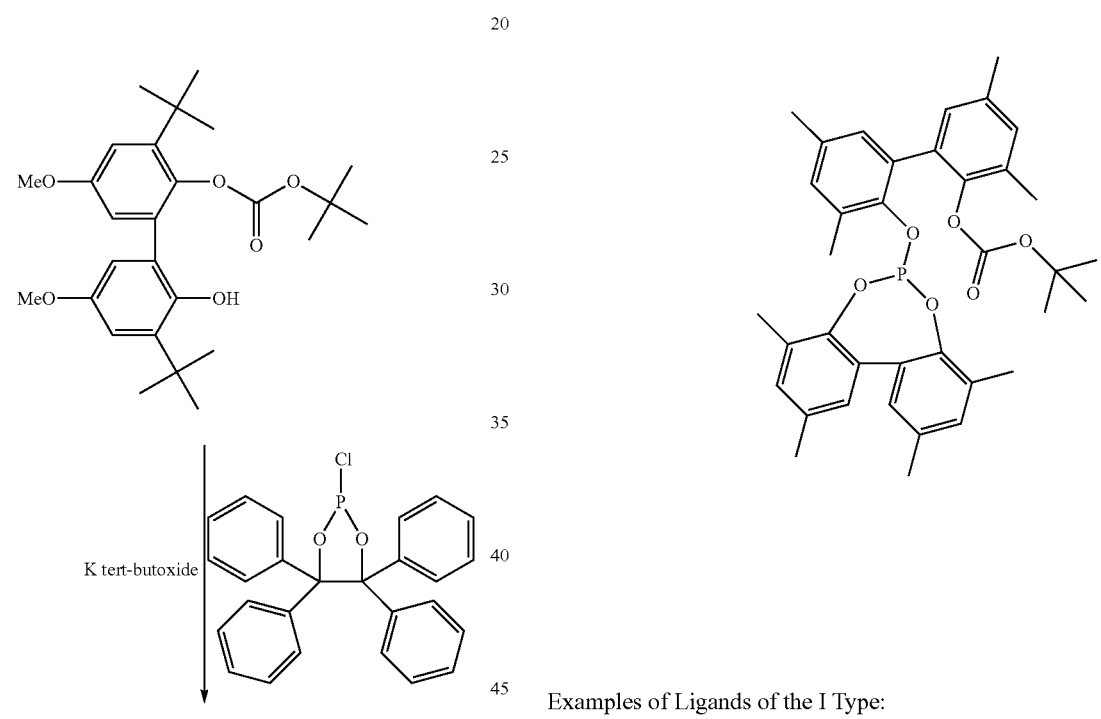
Reaction route C
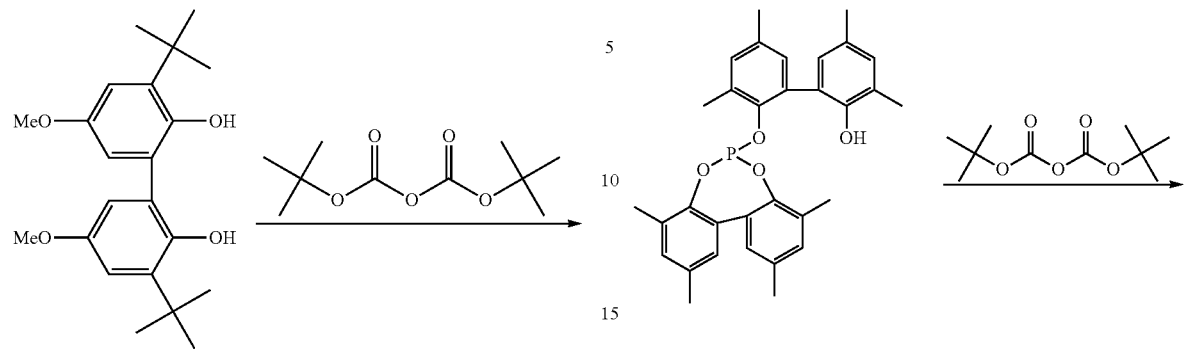
Examples of Ligands of the I Type:
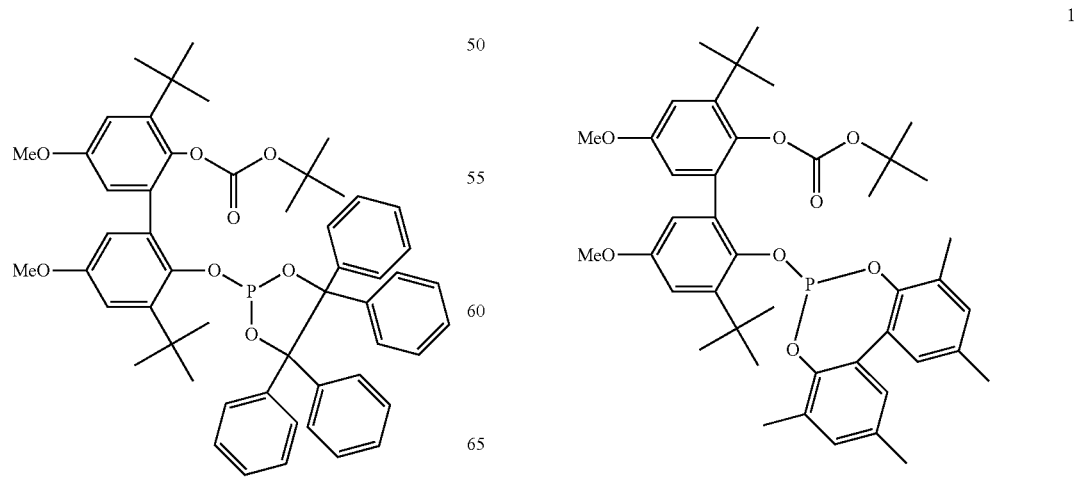

15
-continued
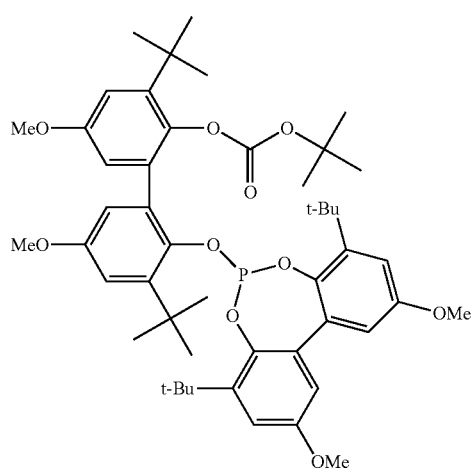
Synthesis of Ligand 1
Reaction Scheme:
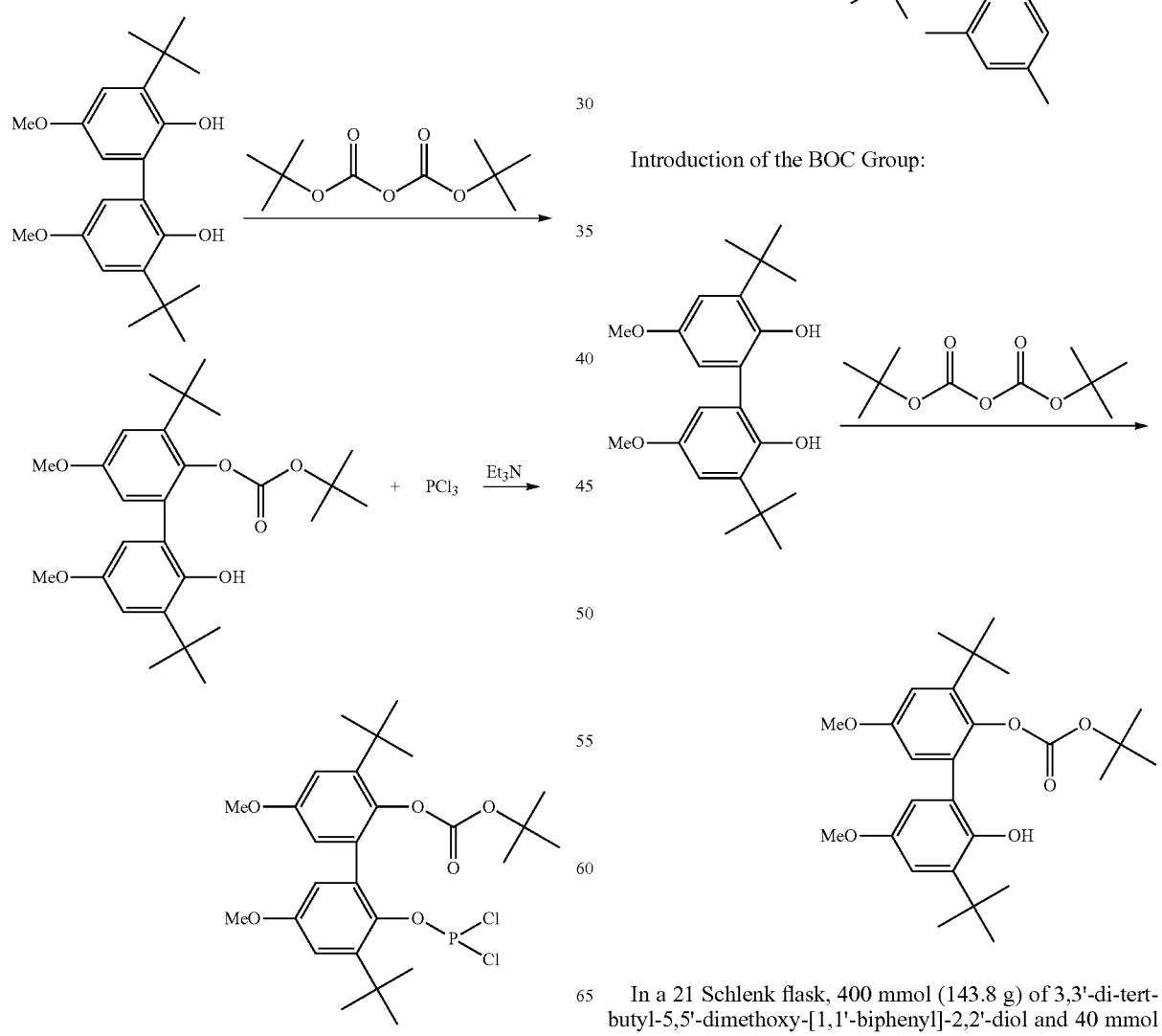
16
-continued
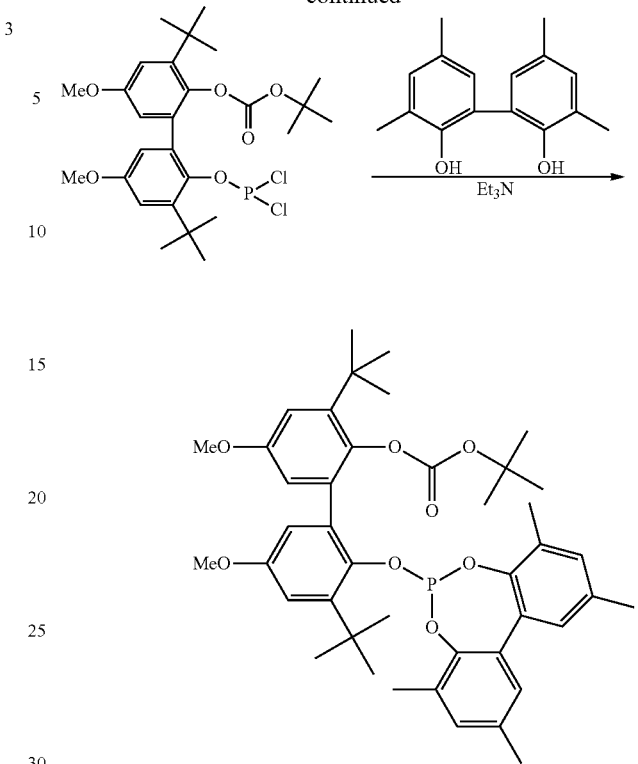
Introduction of the BOC Group:
In a 2 l Schlenk flask, 400 mmol (143.8 g) of 3,3'-di-tert-butyl-5,5'-dimethoxy-[1,1'-biphenyl]-2,2'-diol and 40 mmol (4.8 g) of N,N-dimethylaminopyridine (DMAP) were dissolved in 900 ml of $CH_2Cl_2$. Subsequently, at room temperature, 400 mmol (88 g) of di-tert-butyl dicarbonate were dissolved in 280 ml of $CH_2Cl_2$, transferred to a 500 ml dropping funnel and added dropwise to the biphenol/DMAP solution at 32° C. within one hour. The solution was stirred at room temperature overnight. The next morning, the solvent was removed under reduced pressure. The slightly waxy, reddish residue was admixed with 800 ml of n-heptane and stirred overnight. This gave a white residue which was filtered off, washed twice with 50 ml of n-heptane and then dried. The target product was obtained as a white solid (161.6 g, 84%). $^1$H NMR (toluene-$d_8$): 95% and further impurities.

Reaction of tert-butyl (3,3'-di-tert-butyl-2'-hydroxy-5,5'-dimethoxy-[1,1'-biphenyl]-2-yl)carbonate with phosporous trichloride:

Reaction of tert-butyl (3,3'-di-tert-butyl-2'-((dichlorophosphino)oxy)-5,5'-dimethoxy-[1,1'-biphenyl]-2-yl)carbonate with 3,3',5,5'-tetramethyl-(1,1'-biphenyl)-2,2'-diol

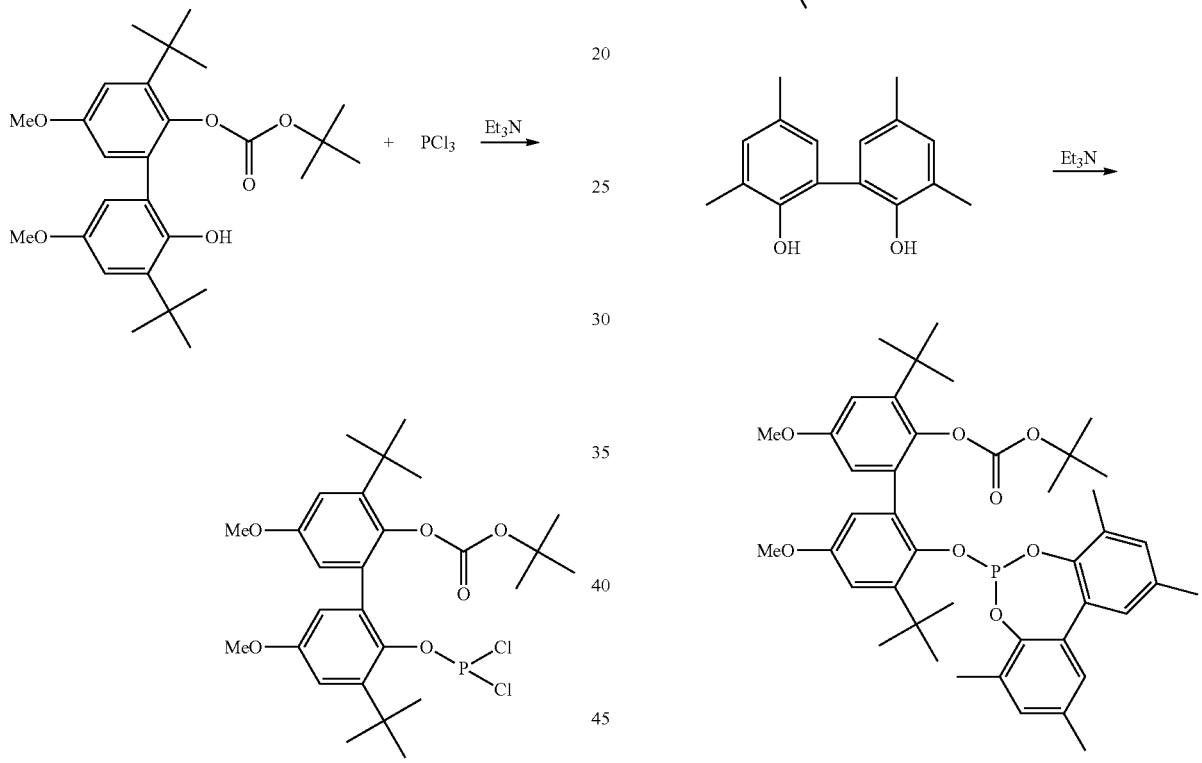

In a 250 ml Schlenk flask which had been repeatedly evacuated and filled with inert gas, 12 g (0.026 mol) of tert-butyl (3,3'-di-tert-butyl-2'-hydroxy-5,5'-dimethoxy-[1,1'-biphenyl]-2-yl)carbonate were dissolved by stirring in 120 ml of dried toluene and 12.8 ml (0.091 mol) of triethylamine.

In a second 500 ml Schlenk flask, 100 ml of dried toluene were first stirred together with 8.1 ml (0.091 mol) of phosphorus trichloride. Subsequently, the phosphorus trichloride-toluene solution was added dropwise to the previously prepared carbonate-amine-toluene solution at room temperature within 30 minutes. On completion of addition, the mixture was heated to 80° C. for 30 minutes and cooled to room temperature overnight.

The next morning, the mixture was filtered, the solids were washed with 50 ml of dried toluene, and the filtrate was concentrated to dryness. The target product was obtained as a solid (13.1 g, 89%). $^{31}$P NMR (202.4 MHz, toluene-$d_8$): 203.2 and 203.3 ppm (100%).

In a 1 l Schlenk flask which had been repeatedly evacuated and filled with inert gas, 24.7 g (0.044 mol) of tert-butyl (3,3'-di-tert-butyl-2'-((dichlorophosphino)oxy)-5,5'-dimethoxy-[1,1'-biphenyl]-2-yl)carbonate were dissolved in 400 ml of acetonitrile.

In a second Schlenk flask (1 l) which had been repeatedly evacuated and filled with inert gas, 10.8 g (0.044 mol) of 3,3',5,5'-tetramethyl-(1,1'-biphenyl)-2,2'-diol were dissolved by stirring in 200 ml of acetonitrile and 13.1 ml (0.011 mol) of dried triethylamine. Subsequently, the chlorophosphite solution was slowly added dropwise to the biphenol-triethylamine solution and the mixture was stirred overnight.

The mixture was then filtered and the residue was washed twice with 15 ml of acetonitrile.

The filtrate was concentrated under reduced pressure until a solid precipitated out. The latter was filtered and dried. The target product was obtained as a white solid (28.5 g, 87%). $^{31}$P NMR (202.4 MHz, toluene-$d_8$): 139.4 ppm (98.5%).

Synthesis of Ligand 3

Reaction of tert-butyl (3,3'-di-tert-butyl-2'-((dichlorophosphino)oxy)-5,5'-dimethoxy-[1,1'-biphenyl]-2-yl)carbonate with 3,3-di-tert-butyl-5,5-dimethoxybiphenol

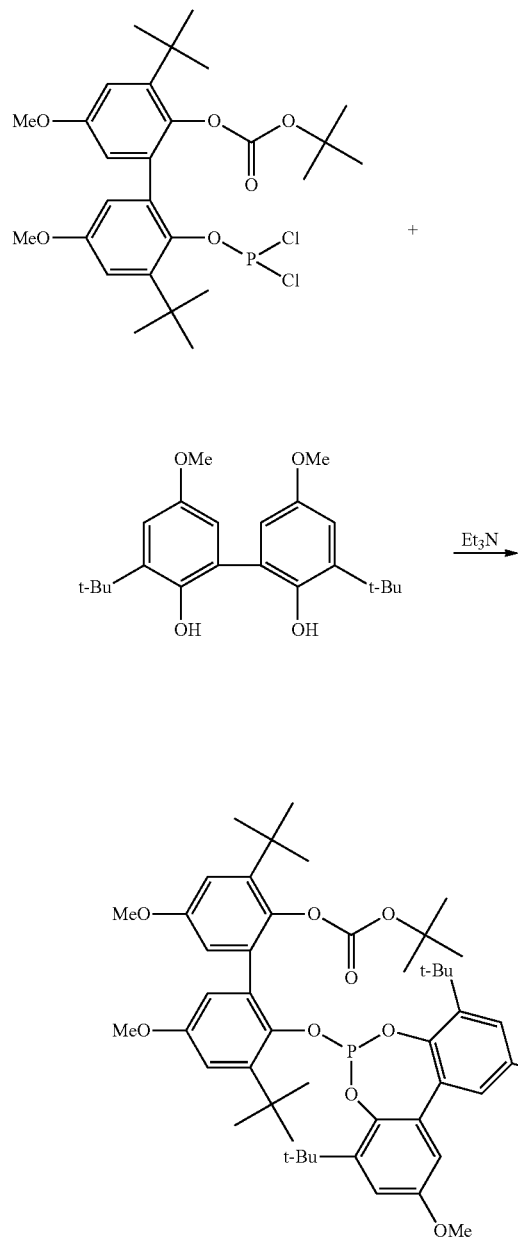

In a 250 ml Schlenk flask which had been repeatedly evacuated and filled with inert gas, 7 g (0.0125 mol) of tert-butyl (3,3'-di-tert-butyl-2'-((dichlorophosphino)oxy)-5,5'-dimethoxy-[1,1'-biphenyl]-2-yl)carbonate were dissolved in 100 ml of dried acetonitrile.

In a second Schlenk flask (100 ml) which had been repeatedly evacuated and filled with inert gas, 4.5 g (0.0125 mol) of 3,3-di-tert-butyl-5,5-dimethoxybiphenol were dissolved in 60 ml of dried acetonitrile and 4.2 ml (0.03 mol) of degassed triethylamine. Subsequently, the biphenol-triethylamine solution was slowly added dropwise at room temperature to the chlorophosphite solution and the mixture was stirred at room temperature overnight.

A portion of the solvent was removed under reduced pressure. The precipitated solids were filtered off and dried. The target product was obtained as a white solid (10.5 g, 96%). $^{31}$P NMR (202.4 MHz, toluene-$d_8$): 140.9 (95.2%) and further impurities (further impurities=P—H compounds, oxide compounds, as yet incompletely converted chlorophosphite).

Procedure for the Catalysis Experiments

Experiment Description—General

In a 100 ml autoclave from Parr Instruments, n-octenes were hydroformylated at 120° C. and synthesis gas pressure 50 bar (CO/$H_2$=1:1 (% by vol.)). As precursor, 0.123 g of Rh(acac)(CO)$_2$ was initially charged for a catalyst concentration of 100 ppm of Rh based on the overall reaction mixture. The solvent used was 40 to 46 g of toluene in each case. Ligand 1 or ligand 2 or the ligand mixture consisting of ligands 1 and 2 was used in different molar excesses relative to rhodium. In addition, as GC standard, about 0.5 g of tetraisopropylbenzene (TIPB) was added. About 6 g of reactant were metered in after the reaction temperature envisaged had been attained.

During the reaction, the pressure was kept constant via synthesis gas regulation with a mass flow meter. The stirrer speed was 1200 min$^{-1}$. Samples were taken from the reaction mixture after 12 hours. The results of the experiments are summarized in Table 1.

(acac=acetylacetonate)

Ligands Used in the Catalysis Experiments:

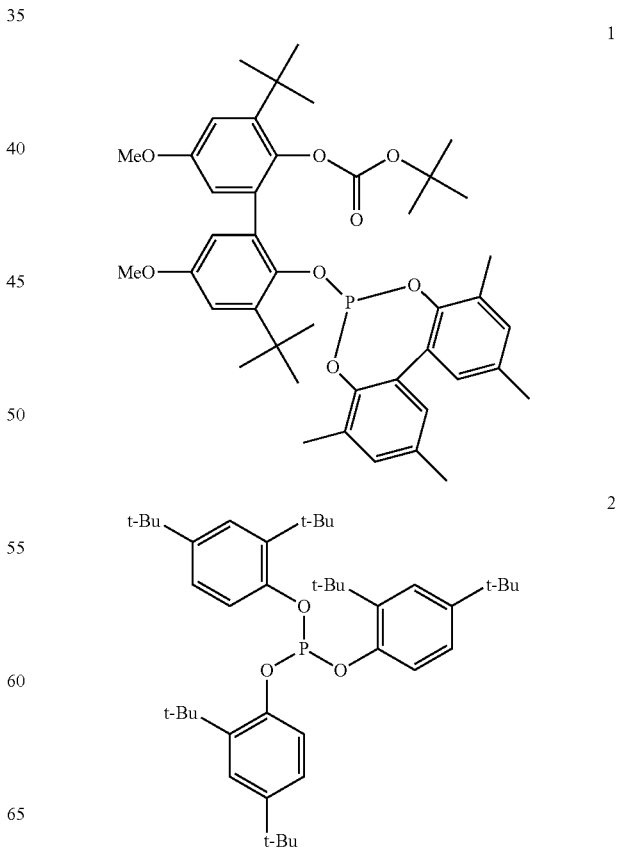

-continued

3

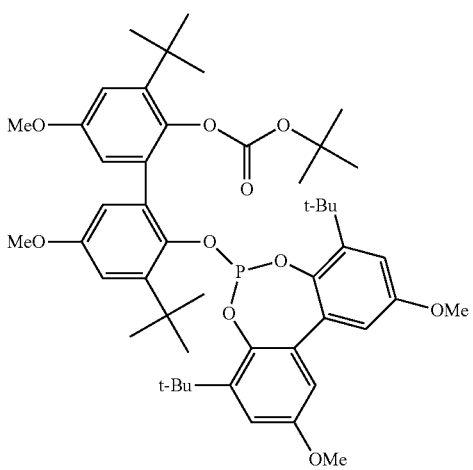

The preparation of ligands 1 and 3 is described in the above experimental section. Ligand 2 (TDTBPP or Alkanox 240) is commercially available.

TABLE 1

| Entry | T in [° C.] | cRh in ppm | P/Rh ligand 1 | P/Rh ligand 2 | Y (total aldehydes + alcohols) in % | S (n-nonanal) in % |
|---|---|---|---|---|---|---|
| 1 | 80 | 90 | 19.8 | 0 | 99.0 | 7.2 |
| 2 | 90 | 90 | 19.8 | 0 | 99.2 | 10.6 |
| 3 | 90 | 280 | 0 | 20.3 | 97.9 | 4.7 |
| 4 | 110 | 90 | 0 | 20.4 | 99.0 | 9.7 |
| 5* | 100 | 90 | 18.8 | 0.8 | 98.7 | 12.0 |
| 6* | 110 | 90 | 18.8 | 0.8 | 97.6 | 17.3 |
| 7* | 110 | 90 | 14.8 | 3.9 | 96.5 | 13.5 |
| 8* | 110 | 90 | 10.0 | 8.1 | 97.9 | 11.4 |
| 9* | 120 | 90 | 18.9 | 0.8 | 95.2 | 22.9 |
| 10* | 120 | 90 | 14.8 | 3.9 | 94.5 | 18.1 |
| 11* | 120 | 90 | 10.0 | 8.1 | 95.5 | 16.5 |
| 12* | 120 | 90 | 5.0 | 11.9 | 95.5 | 15.5 |
| 13* | 120 | 90 | 1.0 | 15.2 | 94.7 | 15.4 |

*inventive mixture or complex mixtures
(Yield = total aldehyde and alcohol yield; S = selectivity for the linear product)

Reaction conditions: synthesis gas pressure 50 bar, substrate: n-octenes

Table 1 contains experiments on the hydroformylation of an n-octene mixture having about 2% 1-octene, 40% 2-octenes, 36% 3-octenes and 23% 4-octenes. Within the series of experiments, mixtures of ligands 1 and 2 with different molar ratios were examined. The first four experiments (entries 1 to 4) are comparative experiments. Only one of the two ligands in each case was used here, i.e. either ligand 1 or ligand 2.

In the experiments which were conducted with inventive mixtures/complex mixtures, it was possible to achieve very good selectivities (S) in each case.

Through the use of inventive mixtures/complex mixtures, it is possible to selectively control the proportion of terminally hydroformylated product. Selectivity for the desired linear aldehydes is much greater here than, for example, in the case of the commercially available ligand 2. It is particularly advantageous in this context that the effects of the two ligands in the mixture enhance one another, and it is necessary to use only as much of the much more expensive ligand 1 as necessary to obtain the desired product selectivity. This constitutes a clear economic advantage over a process regime effected exclusively with the ligand 1.

Table 2 gives the results for the hydroformylation of di-n-butene. Di-n-butene is a mixture of isomers of n-octenes (about 16%), 3-methylheptenes (about 65%) and 3,4-dimethylhexenes (about 19%).

(Yield=total aldehyde and alcohol yield; S=selectivity for the linear product)

TABLE 2

| Entry | Ligand A | Ligand B | P/Rh ligand A | P/Rh ligand B | Y in % | S in % |
|---|---|---|---|---|---|---|
| 1 | — | 2 | — | 20 | 96.9 | 21.8 |
| 2* | 1 | 2 | 14.8 | 5.1 | 82.6 | 27.2 |
| 3* | 3 | 2 | 17.4 | 2.0 | 95.4 | 27.7 |
| 4* | 3 | 2 | 15.7 | 5.1 | 97.0 | 27.5 |
| 5* | 3 | 2 | 10.2 | 10.1 | 96.9 | 25.0 |
| 6* | 3 | 2 | 5.0 | 14.7 | 96.0 | 23.8 |

*inventive mixture or complex mixtures

Reaction conditions: synthesis gas pressure 50 bar, T=140° C., substrate: di-n-butene, P:Rh=20:1; 100 ppm [Rh]

Table 2 contains experiments for hydroformylation of di-n-butene with various mixtures/complex mixtures. Entry 1 contains a comparative experiment which was conducted with ligand 2 only. A good yield was achieved here, but the selectivity leaves something to be desired.

Through the use of the inventive mixtures/complex mixtures, it was possible to increase the selectivity in all cases. Selectivity for the desired linear aldehydes is noticeably greater here than in the case of the commercially available ligand 2.

Through the use of the inventive mixtures/complex mixtures, it is possible to selectively control and increase the proportion of terminally hydroformylated product.

The very expensive ligand 1 can be placed partly by the cheaper ligand 2, which constitutes a significant commercial benefit. The cost/benefit ratio of the ligands used was distinctly improved as a result.

It was thus possible to show, with the aid of the above examples, that the stated problems have been solved through the use of the inventive mixtures/complex mixtures.

German patent application 102014209533.6 filed May 20, 2014, is incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. A mixture, comprising:
at least one of the two compounds of the structures Ia and Ib:

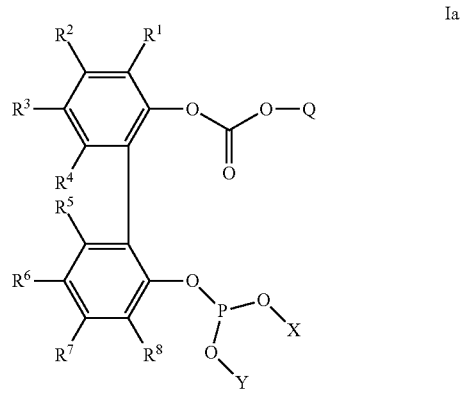

Ia

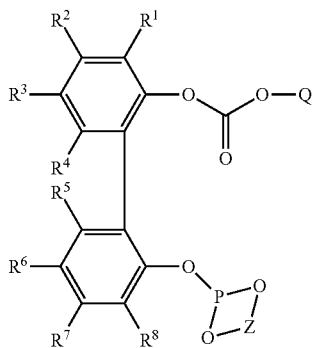

Ib wherein
$R^1$, $R^2$, $R^3$, $R^4$, $R^5$, $R^6$, $R^7$, $R^8$ are each independently selected from the group consisting of:
—H, —($C_1$-$C_{12}$)-alkyl, —O—($C_1$-$C_{12}$)-alkyl, —O—($C_6$-$C_{20}$)-aryl, —($C_6$-$C_{20}$)-aryl, halogen, COO—($C_1$-$C_{12}$)-alkyl, CONH—($C_1$-$C_{12}$)-alkyl, —($C_6$-$C_{20}$)-aryl-CON[($C_1$-$C_{12}$)-alkyl]$_2$, —CO—($C_1$-$C_{12}$)-alkyl, —CO—($C_6$-$C_{20}$)-aryl, —COOH, —OH, —SO$_3$H, —SO$_3$Na, —NO$_2$, —CN, —NH$_2$, and —N[($C_1$-$C_{12}$)-alkyl]$_2$;

X and Y are each independently selected from the group consisting of:
—($C_1$-$C_{12}$)-alkyl, —($C_6$-$C_{20}$)-aryl, —($C_6$-$C_2$O-aryl-($C_1$-$C_{12}$)-alkyl, —($C_6$-$C_{20}$)-aryl-O—($C_1$-$C_{12}$)-alkyl, —($C_1$-$C_{12}$)-alkyl-($C_6$-$C_{20}$)-aryl, —($C_6$-$C_{20}$)-aryl-COO—($C_1$-$C_{12}$)-alkyl, —($C_6$-$C_{20}$)-aryl-CONH—($C_1$-$C_{12}$)-alkyl, —($C_6$-$C_{20}$)-aryl-CON[($C_1$-$C_{12}$)-alkyl]$_2$, —($C_4$-$C_{20}$)-heteroaryl, —($C_4$-$C_{20}$)-heteroaryl-($C_1$-$C_{12}$)-alkyl, and —($C_5$-$C_8$)-cycloalkyl-($C_4$-$C_{20}$)-aryl-CO—($C_6$-$C_{20}$)-aryl, Z is selected from the group consisting of:
—($C_1$-$C_{12}$)-alkyl-, —($C_6$-$C_{20}$)-aryl-, —($C_6$-$C_{20}$)-aryl-($C_1$-$C_{12}$)-alkyl-, —($C_1$-$C_{12}$)-alkyl-($C_6$-$C_2$O-aryl-, —($C_4$-$C_{20}$)-heteroaryl-, —($C_6$-$C_{20}$)-aryl-CO—($C_6$-$C_{20}$)-aryl-, and —($C_6$-$C_{20}$)-aryl-($C_6$-$C_{20}$)-aryl-;

Q is selected from the group consisting of:
—($C_1$-$C_{18}$)-alkyl-, —($C_1$-$C_{18}$)-haloalkyl-, and —NH—($C_1$-$C_{18}$)-alkyl, wherein the alkyl, heteroalkyl, cycloalkyl, heterocycloalkyl, aryl and heteroaryl groups are optionally substituted, and
a compound of the structure IIa:

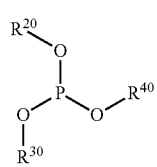

IIa wherein
$R^{20}$, $R^{30}$, $R^{40}$ are each independently selected from the group consisting of:
—($C_1$-$C_{12}$)-alkyl, —($C_6$-$C_{20}$)-aryl, and —($C_3$-$C_{12}$)-cycloalkyl,
two $R^{20}$ and $R^{30}$, or $R^{20}$ and $R^{40}$, or $R^{30}$ and $R^{40}$ radicals are optionally bridged to one another, and optionally have a —($C_6$-$C_{20}$)-aryl-($C_6$-$C_{20}$)-aryl unit, wherein the alkyl, cycloalkyl and aryl groups mentioned are optionally substituted.

2. The mixture according to claim 1, wherein Q is selected from the group consisting of:
—($C_1$-$C_{12}$)-alkyl-, —($C_1$-$C_3$)-alkyl-($C_1$-$C_6$)-aryl-, —($C_1$-$C_{18}$)-haloalkyl-, and —NH—($C_1$-$C_8$)-alkyl.

3. The mixture according to claim 1, comprising at least one of the two compounds of one of the structures Ic and Id:

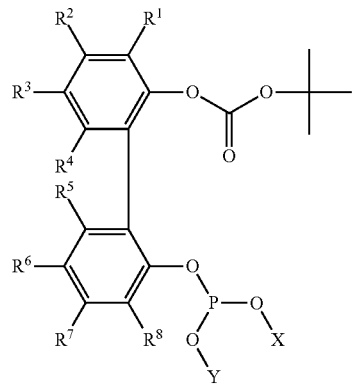

Ic

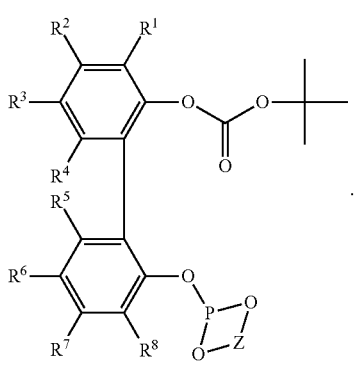

Id

4. The mixture according to claim 1, wherein X and Y are each independently selected from the group consisting of:
—($C_1$-$C_{12}$)-alkyl, —($C_6$-$C_{20}$)-aryl, —($C_6$-$C_{20}$)-aryl-($C_1$-$C_{12}$)-alkyl, —($C_6$-$C_{20}$)-aryl-O—($C_1$-$C_{12}$)-alkyl, and —($C_6$-$C_{20}$)-aryl-COO—($C_1$-$C_{12}$)-alkyl.

5. The mixture according to claim 1, wherein Z is selected from the group consisting of:
—($C_1$-$C_{12}$)-alkyl-, —($C_6$-$C_{20}$)-aryl-, —($C_6$-$C_{20}$)-aryl-($C_1$-$C_{12}$)-alkyl-, —($C_6$-$C_{20}$)-aryl-CO—($C_6$-$C_{20}$)-aryl-, —($C_1$-$C_{12}$)-alkyl-($C_6$-$C_{20}$)-aryl-, and —($C_6$-$C_{20}$)-aryl-($C_6$-$C_{20}$)-aryl-.

6. The mixture according to claim 1, wherein $R^1$, $R^2$, $R^3$, $R^4$, $R^5$, $R^6$, $R^7$, $R^8$ are each independently selected from the group consisting of: —H, —($C_1$-$C_{12}$)-alkyl, —O—($C_1$-$C_{12}$)-alkyl, —O—($C_6$-$C_{20}$)-aryl, —($C_6$-$C_{20}$)-aryl, —COO—($C_1$-$C_{12}$)-alkyl, —CONH—($C_1$-$C_{12}$)-alkyl, —($C_6$-$C_{20}$)-aryl-CON[($C_1$-$C_{12}$)-alkyl]$_2$, —CO—($C_1$-$C_{12}$)-alkyl, —CO—($C_6$-$C_{20}$)-aryl, —COOH, —OH, —NH$_2$, and —N[($C_1$-$C_{12}$)-alkyl]$_2$.

7. The mixture according to claim 1, wherein X and Y are the same radicals.

8. The mixture according to claim 1, comprising a compound of the structure Ie:

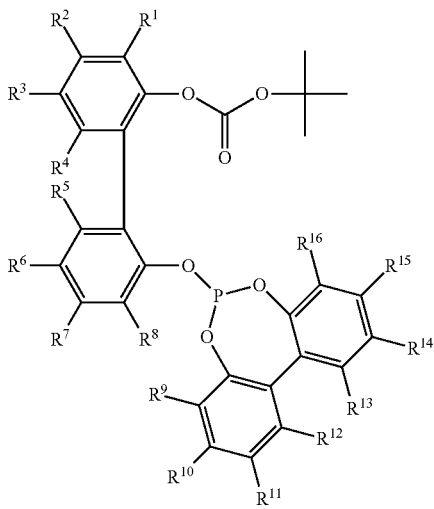

wherein $R^9$, $R^{10}$, $R^{11}$, $R^{12}$, $R^{13}$, $R^{14}$, $R^{15}$, $R^{16}$ are each independently selected from the group consisting of:
—H, —$(C_1$-$C_{12})$-alkyl, —O—$(C_1$-$C_{12})$-alkyl, —O—$(C_6$-$C_{20})$-aryl, —$(C_6$-$C_{20})$-aryl, -halogen, —COO—$(C_1$-$C_{12})$-alkyl, —CONH—$(C_1$-$C_{12})$-alkyl, —$(C_6$-$C_{20})$-aryl-CON[$(C_1$-$C_{12})$-alkyl]$_2$, —CO—$(C_1$-$C_{12})$-alkyl, —CO—$(C_6$-$C_{20})$-aryl, —COOH, —OH, —SO$_3$H, —SO$_3$Na, —NO$_2$, —CN, —NH$_2$, and —N[$(C_1$-$C_{12})$-alkyl]$_2$.

9. The mixture according to claim 1, comprising a compound of the structure If:

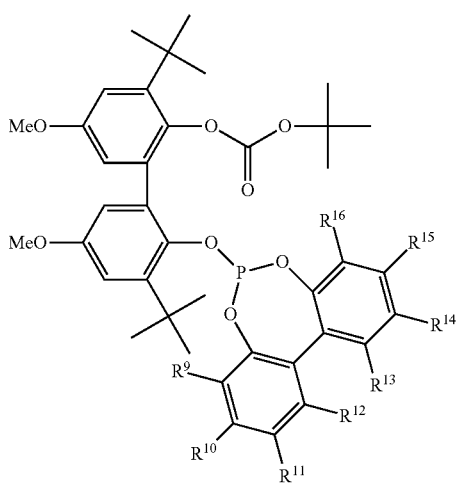

wherein $R^9$, $R^{10}$, $R^{11}$, $R^{12}$, $R^{13}$, $R^{14}$, $R^{15}$, $R^{16}$ are each independently selected from the group consisting of:
—H, —$(C_1$-$C_{12})$-alkyl, —O—$(C_1$-$C_{12})$-alkyl, —O—$(C_6$-$C_{20})$-aryl, —$(C_6$-$C_{20})$-aryl, -halogen, —COO—$(C_1$-$C_{12})$-alkyl, —CONH—$(C_1$-$C_{12})$-alkyl, —$(C_6$-$C_{20})$-aryl-CON[$(C_1$-$C_{12})$-alkyl]$_2$, —CO—$(C_1$-$C_{12})$-alkyl, —CO—$(C_6$-$C_{20})$-aryl, —COOH, —OH, —SO$_3$H, —SO$_3$Na, —NO$_2$, —CN, —NH$_2$, and —N[$(C_1$-$C_{12})$-alkyl]$_2$.

10. The mixture according to claim 1, wherein $R^{20}$, $R^{30}$, $R^{40}$ each independently selected from the group consisting of:
—$(C_1$-$C_{12})$-alkyl, and —$(C_6$-$C_{20})$-aryl,
wherein the alkyl and aryl groups mentioned are optionally substituted.

11. The mixture according to claim 1, comprising a compound of the structure IIb:

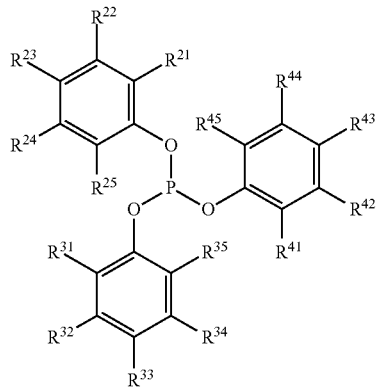

wherein
$R^{21}$, $R^{22}$, $R^{23}$, $R^{24}$, $R^{25}$, $R^{31}$, $R^{32}$, $R^{33}$, $R^{34}$, $R^{35}$, $R^{41}$, $R^{42}$, $R^{43}$, $R^{44}$, $R^{45}$ are each independently selected from the group consisting of:
—H, —$(C_1$-$C_{12})$-alkyl, —O—$(C_1$-$C_{12})$-alkyl, —O—$(C_6$-$C_{20})$-aryl, —$(C_6$-$C_{20})$-aryl, -halogen, —COO—$(C_1$-$C_{12})$-alkyl, —CONH—$(C_1$-$C_{12})$-alkyl, —$(C_6$-$C_{20})$-aryl-CON[$(C_1$-$C_{12})$-alkyl]$_2$, —CO—$(C_1$-$C_{12})$-alkyl, —CO—$(C_6$-$C_{20})$-aryl, —COOH, —OH, —SO$_3$H, —SO$_3$Na, —NO$_2$, —CN, —NH$_2$, and —N[$(C_1$-$C_{12})$-alkyl]$_2$.

12. The mixture according to claim 11, wherein $R^{21}$, $R^{22}$, $R^{23}$, $R^{24}$, $R^{25}$, $R^{31}$, $R^{32}$, $R^{33}$, $R^{34}$, $R^{35}$, $R^{41}$, $R^{42}$, $R^{43}$, $R^{44}$, $R^{45}$ are each independently selected from the group consisting of:
—H, —O—$(C_1$-$C_{12})$-alkyl, —O—$(C_6$-$C_{20})$-aryl, and —$(C_6$-$C_{20})$-aryl.

13. The mixture according to claim 1, wherein compound Ia is present.

14. The mixture according to claim 1, wherein compound Ib is present.

15. The mixture according to claim 3, wherein compound Ic is present.

16. The mixture according to claim 3, wherein compound Id is present.

17. A complex mixture, comprising:
the mixture according to claim 1, and
a metal atom selected from the group consisting of Rh, Ru, Co, and Ir.

18. A process of hydroformylating an olefin, comprising:
a) initially charging an olefin;
b) adding
the complex mixture according to claim 17, or
a mixture according to claim 1 and a compound comprising a metal atom selected from the group consisting of Rh, Ru, Co, and Ir, to obtain a reaction mixture;
c) feeding $H_2$ and CO into the reaction mixture,
d) heating the reaction mixture, to obtain conversion of the olefin to an aldehyde.

19. The process according to claim 18, wherein said olefin is a branched, unbranched, terminal or internal olefin.

20. The process according to claim 18, wherein said aldehyde is a linear aldehyde.

* * * * *